(12) United States Patent
Otts et al.

(10) Patent No.: US 11,672,649 B2
(45) Date of Patent: Jun. 13, 2023

(54) ELECTROWETTING OPHTHALMIC DEVICES INCLUDING AN ELASTIC ELECTRODE

(71) Applicant: Verily Life Sciences LLC, South San Francisco, CA (US)

(72) Inventors: Daniel B. Otts, Pleasanton, CA (US); Stein Kuiper, South San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

(21) Appl. No.: 17/163,898

(22) Filed: Feb. 1, 2021

(65) Prior Publication Data

US 2021/0154003 A1 May 27, 2021

Related U.S. Application Data

(63) Continuation of application No. 15/944,298, filed on Apr. 3, 2018, now Pat. No. 10,905,545.

(Continued)

(51) Int. Cl.
*A61F 2/16* (2006.01)
*G02C 7/08* (2006.01)
(Continued)

(52) U.S. Cl.
CPC .......... *A61F 2/1635* (2013.01); *A61L 31/022* (2013.01); *A61L 31/06* (2013.01);
(Continued)

(58) Field of Classification Search
CPC combination set(s) only.
See application file for complete search history.

(56) References Cited

U.S. PATENT DOCUMENTS

| 5,987,361 A | 11/1999 | Mortimer |
| 7,684,016 B1 | 3/2010 | Schaefer |

(Continued)

FOREIGN PATENT DOCUMENTS

| CN | 101395495 A | 3/2009 |
| CN | 102221716 A | 10/2011 |

(Continued)

OTHER PUBLICATIONS

Dhindsa, M. et al., "Electrowetting without Electrolysis on Self-Healing Dielectrics", Langmuir, Apr. 2011, 7 pages.

(Continued)

*Primary Examiner* — Javier G Blanco
(74) *Attorney, Agent, or Firm* — Christensen O'Connor Johnson Kindness PLLC

(57) ABSTRACT

Ophthalmic devices having elastic electrodes are disclosed herein. An example ophthalmic device may be an intraocular lens that includes a support structure, two optical windows, two immiscible fluids, and an elastic electrode. The support structure may have an inner surface defining an aperture with first and second optical windows disposed on opposite sides of the support structure and spanning the aperture. The two immiscible liquids may be disposed in a cavity formed by the aperture and the first and second optical windows, and the elastic electrode may be disposed on the inner surface. The elastic electrode may be formed from an elastic metal alloy having a minimum yield strain of 0.25%.

12 Claims, 5 Drawing Sheets

Related U.S. Application Data

(60) Provisional application No. 62/502,039, filed on May 5, 2017.

(51) Int. Cl.

| | | |
|---|---|---|
| *G02B 3/14* | (2006.01) | |
| *G02B 26/00* | (2006.01) | |
| *A61L 31/02* | (2006.01) | |
| *A61L 31/06* | (2006.01) | |
| *A61L 31/08* | (2006.01) | |
| *G02B 7/02* | (2021.01) | |
| *A61F 2/48* | (2006.01) | |

(52) U.S. Cl.
CPC .............. *A61L 31/088* (2013.01); *G02B 3/14* (2013.01); *G02B 26/005* (2013.01); *G02C 7/085* (2013.01); *A61F 2/482* (2021.08); *A61F 2210/0014* (2013.01); *A61F 2250/0001* (2013.01); *A61F 2250/0002* (2013.01); *A61F 2250/0003* (2013.01); *A61F 2250/0018* (2013.01); *A61F 2250/0056* (2013.01); *G02B 7/02* (2013.01)

(56) References Cited

U.S. PATENT DOCUMENTS

| | | |
|---|---|---|
| 8,157,797 B2 | 4/2012 | Boukhny et al. |
| 8,448,250 B2 | 7/2013 | Nibauer et al. |
| 9,414,908 B2 | 8/2016 | Maillard |
| 2006/0256448 A1* | 11/2006 | Oh .................. G02B 26/005 359/666 |
| 2007/0133103 A1 | 6/2007 | Stempel et al. |
| 2008/0288036 A1 | 11/2008 | Greenberg et al. |
| 2010/0179544 A1 | 7/2010 | Boukhny et al. |
| 2012/0026596 A1 | 2/2012 | Berge et al. |
| 2012/0050880 A1 | 3/2012 | Pugh et al. |
| 2012/0238857 A1 | 9/2012 | Wong et al. |
| 2012/0310339 A1 | 12/2012 | Berge |
| 2013/0152386 A1 | 6/2013 | Pandojirao-S et al. |
| 2013/0229618 A1 | 9/2013 | Otts et al. |
| 2013/0245754 A1 | 9/2013 | Blum et al. |
| 2014/0002789 A1 | 1/2014 | Pugh et al. |
| 2014/0002790 A1* | 1/2014 | Pugh ...................... G02C 7/04 351/159.39 |
| 2014/0253870 A1 | 9/2014 | Jiang et al. |
| 2014/0347741 A1 | 11/2014 | Karam et al. |
| 2014/0350554 A1 | 11/2014 | Keller |
| 2016/0062147 A1 | 3/2016 | Pugh et al. |
| 2016/0259094 A1 | 9/2016 | Aschwanden et al. |

FOREIGN PATENT DOCUMENTS

| | | |
|---|---|---|
| CN | 105632766 A | 6/2016 |
| EP | 1798578 A1 | 6/2007 |
| EP | 3048472 A1 | 1/2008 |
| EP | 2947496 A1 | 11/2015 |
| JP | 2009519479 A | 5/2009 |
| JP | 2010517081 A | 5/2010 |
| WO | 2007/107589 A1 | 9/2007 |

OTHER PUBLICATIONS

International Search Report and Written Opinion from the International Searching Authority dated Sep. 10, 2018, for International Application No. PCT/US2018/030247, filed Apr. 30, 2018, 16 pages.
Office Action dated May 22, 2020, for Chinese Patent Application No. 201880029514.6. (17 pages).
Japanese Office Action dated Dec. 2, 2021, issued in JP Application No. 2019-555494 filed on Dec. 3, 2019, 2 pages.

* cited by examiner

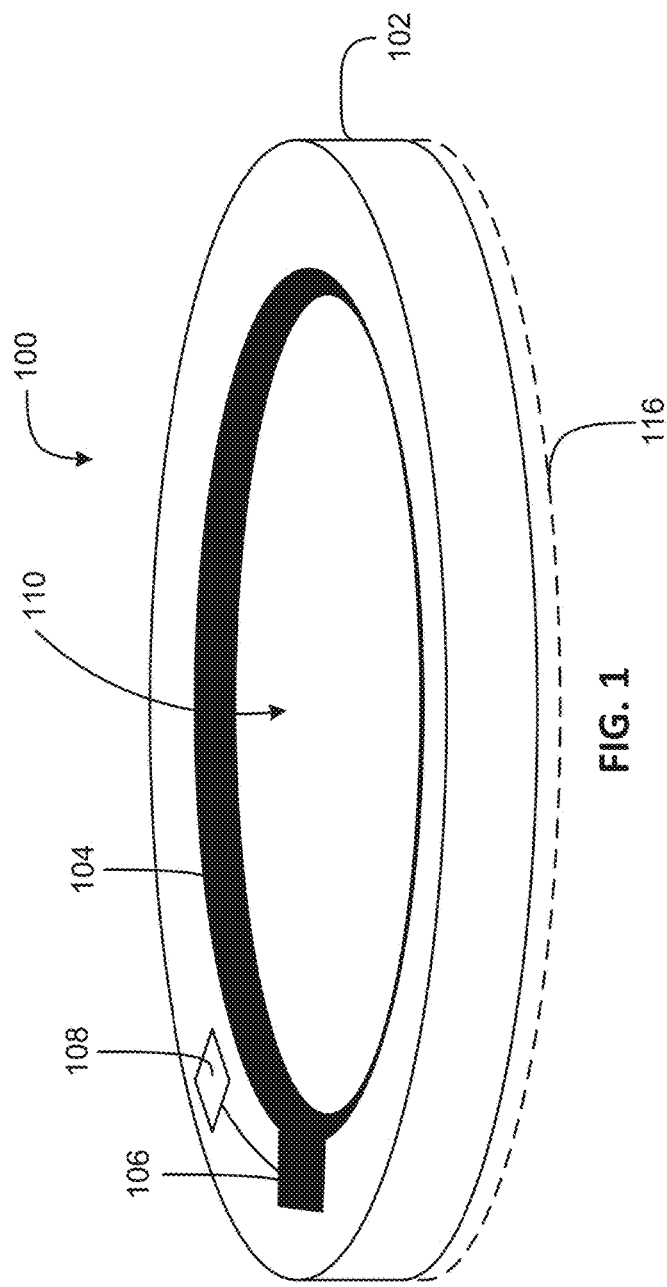
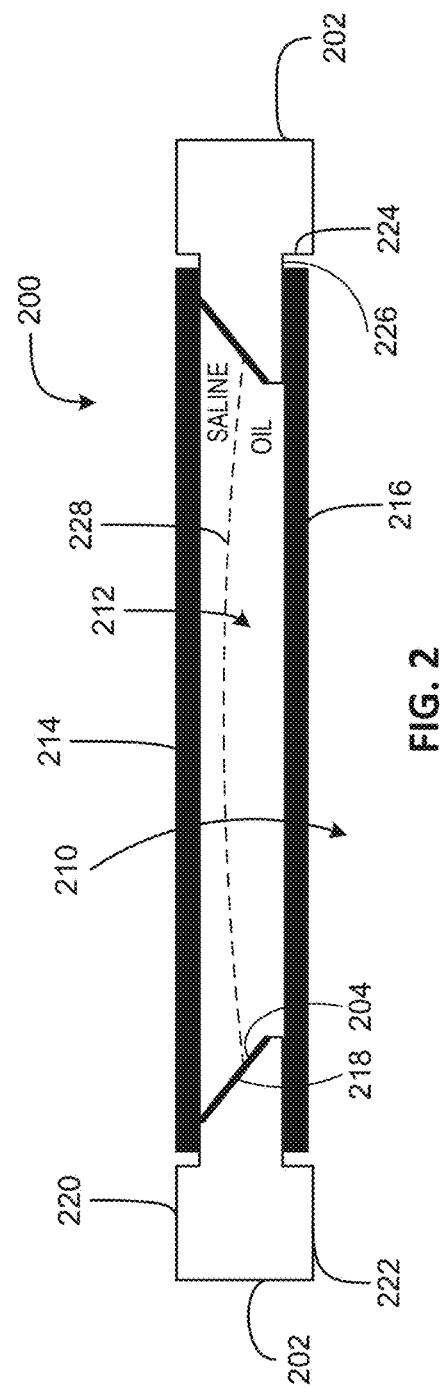
FIG. 1
FIG. 2

ELECTROWETTING OPHTHALMIC DEVICES INCLUDING AN ELASTIC ELECTRODE

CROSS-REFERENCE TO RELATED APPLICATIONS

This application is a continuation of U.S. patent application Ser. No. 15/944,298, filed Apr. 3, 2018, which claims the benefit of U.S. Provisional Application No. 62/502,039, filed May 5, 2017, which are hereby incorporated by reference in their entireties.

TECHNICAL FIELD

This disclosure relates generally to ophthalmic devices, and, in particular but not exclusively, relates to electrowetting ophthalmic devices including an elastic electrode.

BACKGROUND INFORMATION

Presbyopia treatment may include implantation of a replacement lens. Such lenses, which may also be referred to as intraocular lenses, may provide static or dynamic accommodation, or a combination thereof. Various techniques may be available to provide dynamic accommodation, such as mechanical or electrical controlled accommodation. The accommodation may be provided by actuation of a dynamic optical component that provides multiple levels of optical power. The change in optical power may provide different focal distances to the user via the intraocular lens. The amount of actuation, however, may depend on the technique used, e.g., mechanical or electrical.

If electrical actuation is used, the electronics and conductors may need to meet certain requirements that relate to visibility, implantation compatibility, and the implantation procedures. For example, it may be desirable to have some or all of the electronics and/or conductors to be elastic, and further formed from materials amenable to use in or on the eye.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIG. 1 is an illustration of an intraocular lens including an elastic electrode in accordance with an embodiment of the disclosure.

FIG. 2 is a cross-sectional illustration of an intraocular lens including an elastic electrode in accordance with an embodiment of the disclosure.

DETAILED DESCRIPTION

Figure 3:
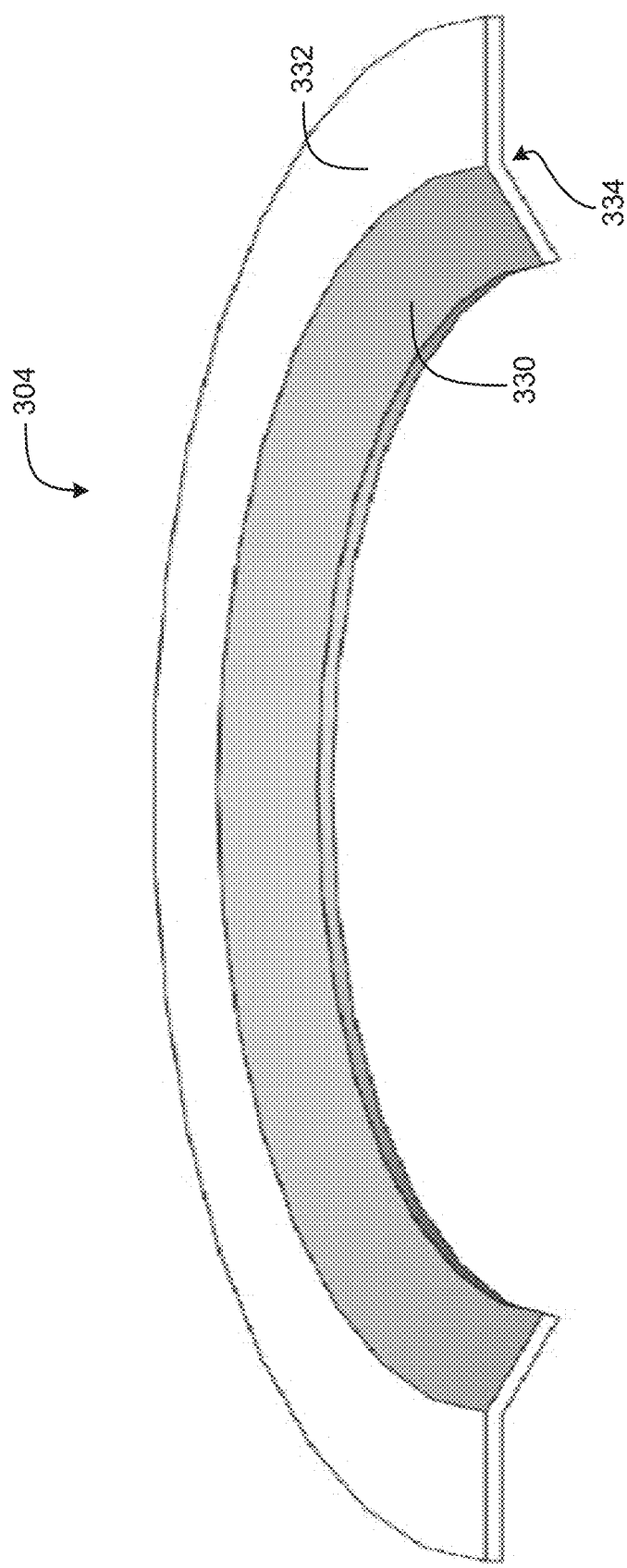
FIG. 3 is a cross-sectional illustration of an electrode in accordance with an embodiment of the disclosure.

Embodiments of an apparatus and method for an intraocular lens having an elastic electrode are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

An intraocular lens (IOL) may be implanted in a user's eye to assist in accommodation when the user's lens is no longer able to change focus as desired, for example. The IOL may have static optical power or may have the ability to dynamically accommodate, e.g., alter the optical power of the IOL, so the user may change focus similar to the natural eye. Dynamic accommodation, however, may require an IOL that is capable of changing the shape of an internal lens, for example.

One technique of interest is for providing dynamic accommodation is electrowetting. Electrowetting operates by changing a surface energy of an electrode from hydrophobic to hydrophilic when bias is applied, and vice versa, for example, which may cause an interface between two immiscible liquids of different index of refraction to change shape, thereby providing a lensing effect. A voltage applied to the electrode may attract one of the two immiscible liquids, which causes the change to the shape of the interface. The surface energy of the electrode may additionally be affected or established by a dielectric and/or polymer layer disposed on the electrode, for example.

Additionally, because the IOL will be implanted into the eye, a small incision in the eye may be desirable. Yet, because the IOL may be of the same size as the original lens, for example, a large incision may be required. However, if the IOL is capable of being rolled up into a cylindrical shape or folded, a smaller incision may be possible. In general, most of the materials forming the IOL are amenable to being rolled or folded, but conventional conductors may experience reliability issues due to the stresses of rolling/flexing events. For example, conventional conductors may delaminate from a substrate and/or crack and/or buckle from the stresses induced from rolling. Accordingly, it may further be desirable for the conductor to be flexible and deformable, e.g., elastic, and further desirable for the conductor, e.g., electrode, to return to a desired shape upon unrolling/unfolding without experiencing inelastic deformation.

It should be noted that while the herein discussion may be centered on IOLs that such discussion is not intended to be limiting, and the aspects of the disclosure are equally applicable to on-eye wearable ophthalmic devices. In general, the features of the disclosure are directed toward elastic electrodes for devices that may experience bending and/or rolling that may damage inelastic electrodes, for example.

FIG. 1 is an illustration of an intraocular lens 100 including an elastic electrode in accordance with an embodiment of the disclosure. The illustrative embodiment of the IOL 100 includes a support structure 102, an electrode 104, a contact 106, control electronics 108, and an optical window 116. In general, the IOL 100 may include other components, such as a second optical window (disposed on the opposite side of the support structure 102 from the optical window 116), and a dynamic optic which are not shown in FIG. 1. In some embodiments, the IOL 100 will provide dynamic accommodation to a user based on electrowetting principles. For example, the IOL 100 may include two immiscible fluids, such as an oil and an electrolyte, that may provide dynamic accommodation by inducing a change in the shape of an interface between the two immiscible fluids in response to an applied voltage. The change in shape of the liquid interface may provide a lensing behavior. In the illustrated embodiment of the IOL 100, the electrode 104 provides a conductor for applying the voltage to induce the lensing behavior.

The support structure 102 may provide mechanical support for the various features of the IOL 100. For example, the support structure 102 may be a substrate for the electrode 104, the contact 106, the control electronics 108, the optical window 116, and various other components discussed herein. In general, the support structure 102 may be formed from a biocompatible material that is amenable to implantation into an eye. Example materials may include silicones, sol-gels, and AcrySof®. Other biocompatible materials, such as biocompatible hydrogel, hydrophobic acrylic, fluorinated polymethacrylate and/or the like, may also be used. The support structure 102 may be a main structural component of the IOL 100 that provides a platform for other IOL 100 components. The support structure 102 may be flexibly capable of being rolled up and/or folded so that it may be manipulated into a smaller shape to accommodate insertion into an eye through a small incision, e.g., an incision roughly 2 mm in length. It is preferably highly elastic, so that it will return to its original shape after unfolding.

In some embodiments, the support structure 102 is also a substrate for mounting various electronics, such as the control electronics 108. The control electronics 108 may be coupled to at least provide a voltage to the electrode 104. While the control electronics 108 is depicted as being mounted to a surface of the support structure 102, in some embodiments, the control electronics 108 are tethered to the support structure 102 and coupled to the contact 106. In such an embodiment, the control electronics 110 may be mounted to a separate support structure, such as a substrate formed from a biocompatible material, and implanted in a different area of an eye than the IOL 100. In the illustrated embodiment of the IOL 100, the support structure 102 is annulus-shaped, e.g., washer-shaped, having an opening 110, e.g., an aperture, formed therethrough. The opening 110 may provide an optical path for the IOL 100. In some embodiments, the optical window 116, along with a second optical window (not shown in FIG. 1) are be placed over the opening 110 on both a top and bottom surface of the support structure 102 (see FIG. 2 for an example). The optical windows may provide a boundary for the immiscible fluids and retain them in the opening 110.

The opening 110 may be formed by an inner surface, e.g., a sidewall, of the support structure 102. In the illustrated embodiment of the IOL 100, the sidewall includes the electrode 104 disposed thereon. While the sidewall may define the opening 110, the electrode 104 may be exposed to the immiscible fluids disposed therein. The sidewall may be at a non-orthogonal angle, e.g., oblique angle, to top and/or bottom surfaces of the support structure 102. For example, the sidewall may be at a 45° angle to at least one of the top or bottom surfaces of the support structure 102. In general, performance aspects of the IOL 100 may determine an oblique angle the sidewall may be at with respect to a top or bottom surface of the support structure 102, and other angles other than 45° are within the scope of the present disclosure. In some embodiments, the shape of the sidewall forms a conical frustum.

The electrode 104 may be disposed on the sidewall of the support structure 102. In some embodiments, it may be desirable that the electrode 104 be elastic and return to a desired shape upon rolling and unrolling or folding/unfolding. To obtain such qualities, the electrode 104 may be formed from materials that may be deformed, rolled up, or have a large degree of flexibility without negatively affecting their electrical and/or mechanical properties upon unrolling, unfolding, etc. In general, it may be desirable for the material to withstand a large amount of deformation, e.g., rolling/bending, without resulting in inelastic deformation and/or the formation of kinks and cracks. To obtain such characteristics, the material should have a high yield strain, with minimum yield strain ranging from 0.25% to 5%, or greater. Example materials may include spring steel or one or more shape memory alloys. The spring steel may be 301 spring-tempered stainless steel, for example, and the shape memory alloy may be nickel-titanium (Nitinol), but other shape memory alloys may also be implemented. In some embodiments, the electrode 104 is pre-formed from a desired elastic or superelastic metal alloy and incorporated into the support structure during formation of the IOL 100. In some embodiments, the electrode 104 may be stamped from a foil of the desired metal alloy, or machined from stock of the desired alloy. In some embodiments, the electrode 104 is incorporated into the support structure 102 during molding of the same.

In some embodiments, the electrode 104 is encapsulated in one or more dielectrics. For example, a dielectric layer may be formed over at least the electrode 104 to prevent electrolysis, provide durability, protection from other components, and mechanical support. The dielectric layer may be formed from a polymer, and it may be desirable that the dielectric provide a conformal coating. An example polymer may be Parylene-C®, Parylene-N, Parylene-D, Parylene-HT, and Parylene-AF4. In some embodiments, the dielectric layer is encapsulated by a surface energy changing layer, such as a fluoropolymer for example.

The contact 106 may be part of the electrode 104, and disposed on a surface of the support structure 102, such as a top surface or a bottom surface. In the illustrated embodiment of IOL 100, the contact 106 is shown on a top surface. The contact 106 may provide a contact point for providing voltage to the electrode 104, for example. However, the contract 106 does not need to be part of the electrode 104, and may be a separate component.

In general, the electrode 104 may be energized with a voltage to induce electrowetting in the IOL 100, such as by the control electronics 108. The voltage on the electrode 104 may cause a change to the surface energy of the electrode 104 and/or one or more dielectric layers disposed on the electrode 104. The change in surface energy may cause the surface to change from hydrophilic to hydrophobic, or vice versa. The change in surface energy may cause one or more liquids in the aperture to change shape, which may affect an optical power of the IOL 100.

FIG. 2 is a cross-sectional illustration of an intraocular lens 200 including an elastic electrode in accordance with an embodiment of the disclosure. The IOL 200 may generally be similar to the IOL 100. The illustrated example of the IOL 200 includes a support structure 202, an electrode 204, first and second optical windows 214 and 216, and two or more immiscible fluids 212. The IOL 200 may provide dynamic accommodation to a user induced by electrowetting principles.

The support structure 202 may be annulus-shaped and have an aperture 210 formed therethrough. A sidewall 218 of the support structure 202 may at least partially form the aperture 210, along with other internal facets of the support structure 202. The support structure 202 may provide structural support for the electrode 204, one or more contact pads (not shown) of the electrode 204, and the optical windows 214, 216. Additionally, the support structure 202 may provide a substrate for electronics and/or power sources for providing charge to at least the electrode 204 to induce the electrowetting-based dynamic accommodation of the IOL 200.

The support structure 202 may further have a recess formed on an inner edge on both the top and bottom surfaces 220, 222, respectively, that encircles the aperture 210. The recesses may provide a surface for mounting and sealing the optical windows 214, 216 to the support structure 202. The recess may be defined by surfaces 224 and 226 formed into the bottom surface 222, which may be mirrored on the top surface 220. In some embodiments, the recess formed into the top surface 220 and the recess formed into the bottom surface 222 may be different and provide different surface areas of the support structure 202. Additionally, the sidewall 218, which extends from recessed top and bottom surfaces of the support structure 202 may be truncated at an innermost point that defines the smallest diameter of the aperture 210. Of course, the support structure 202 may be formed without the surfaces 224 and 226 and the optical windows 214 and 216 may, instead, be disposed on the top and bottom surfaces 220 and 222, respectively.

The support structure 202 may be formed from one or more biocompatible materials, such as silicone, sol-gels, polymers, and the like. For example, the support structure 202 may be formed from AcrySof produced by Alcon of Fort Worth, Tex. The biocompatible material may be amenable to implantation in an eye allowing the IOL 200 to be implanted into the eye of a user. Additionally, the support structure 202 may be transparent so not to affect a user's vision after implantation.

The first and second optical windows 214, 216 may be mounted to top and bottom sides of the support structure 202. The first and second optical windows 214, 216 may be formed from transparent or partially transparent polymerics or thin glass. Example polymerics include Polydimethylsiloxane, hydrophobic acrylic (e.g., AcrySof), of silicones, acrylics, epoxies, urethanes, combinations thereof, and the like. While top and bottom are used herein to discuss the opposite sides of the support structure 202, the top and bottom designations do not notate any directionality to the IOL 200 and are used merely as a reference with respect FIG. 2. The optical windows 214, 216 may be transparent and disposed to cover the aperture 210. The optical windows 214, 216 may be with or without optical power. In some embodiments, one or both of the optical windows provides static optical power to the IOL 200, which may be affected by the electrowetting-based dynamic accommodation of the IOL 200. In some embodiments, the optical windows 214, 216 do not have any optical power. In either embodiment, the optical windows 214, 216 may be coupled to the support structure 202 to retain the two immiscible fluids 212 within a cavity. The cavity may be formed by the support structure 202 and the optical windows 214, 216, with the electrode 204 exposed to the cavity.

Additionally, one of the optical windows may also be conductive. For example, the optical window 214, which the inner surface 218 faces, is conductive. A transparent conductor, such as indium tin oxide (ITO) may be deposited on the optical window 214, for example. Having the optical window 214 conductive may allow a potential difference to be formed between the electrode 204 and the optical window 214, which may be used to apply the electrowetting-induced accommodation.

The two immiscible fluids 212 may be disposed within the cavity, and due to their immiscibility an interface 228 may be formed between the two. The interface may form the dynamic optic of the IOL 200. For example, potential differences between the electrode 204 and the optical window 214 may cause the interface 228 at the electrode 204 to move up or down the face of the electrode 204. The movement of the interface 228 may change a shape of the interface, which, in turn, may change an optical power of the IOL 200. The two immiscible fluids 212 may have different index of refraction, which provides the lensing function. Examples of the two immiscible fluids 212 may be oil and saline.

The electrode 204 may be formed from an elastic, superelastic, or pseudoelastic metal alloy. It may be desirable that the metal alloy have a minimum yield strain of 0.25%, although 0.5% is preferred in some embodiments, and 5% or greater is preferred in yet other embodiments. In some embodiments, the electrode 204 is formed from spring steel, which has a yield strain of 0.25%, or a shape-memory alloy. For example, the shape-memory alloy may be Nitinol (nickel-titanium alloy) of various compositions, which has a yield strain of a 5% or greater, copper-zinc-aluminum, copper-aluminum, copper-aluminum-nickel, or copper-aluminum-beryllium. In embodiments that include Nitinol, the surface of the electrode 204 may be finished, e.g., coated with, a valve metal layer. Additionally, the valve metal-coated electrode 204 may further be anodized in some embodiments. An example valve metal may be titanium, but other valve metals are also contemplated by this disclosure, such as zirconium, hafnium, and tantalum (e.g., IVB and VB elements). In other embodiments, it may be desirable to form the electrode 204 out of a biocompatible elastic metal alloy, such as a medical grade titanium having high elasticity. For example, the medical grade titanium may be Ti6A14V.

In some embodiments, the electrode 204 is pre-formed and disposed on the sidewall 218 during or after formation of the support structure 202. The pre-formed electrode 204 may have a thickness of 5 to 100 microns, depending on material. The electrode 204 may additionally include a flange extending from one edge with the flange disposed on at least a portion of the surface 226 that forms the recess. The flange, which may form a complete circle around the electrode 204 or just form a tab, may be disposed on the surface 226 on either the top or bottom side of the support structure 202.

Additionally, the IOL 200 may be folded or rolled up for insertion into a user's eye without experiencing inelastic deformation upon unfolding/unrolling. A radius of bending or rolling may also affect the desired thickness of the electrode 204. It may be desirable that the electrode 204 not plastically deform after rolling or bending and that it returns to a desired shape without any kinks or cracks formed thereon/therein, which may be dependent upon the yield strain of the metal alloy used to form the electrode 204. Kinks and cracks may affect the electrowetting action, which may adversely affect the lensing effect.

In some examples, there may be two or more polymer-based conformal layers encapsulating the electrode 204. In embodiments having two polymer-based dielectric layers, the dielectric layer in contact with the electrode 204 may provide durability, protection and mechanical support, whereas the second dielectric layer may provide an external surface having a different surface energy. Example dielectrics may include Parylene(s), silicones, and Fluoropolymers.

As shown in FIG. 2, the sidewall 218 of the support structure 202 is at an oblique angle to top and bottom surfaces 220, 222, respectively, of the support structure 202. In some embodiments, the inner surface 218 is shaped like a conical frustum. In some embodiments, the inner surface 218 is at 45° to top and bottom surfaces of the support structure 202. However, the angle of the inner surface 218 to the top and/or bottom surfaces of the support structure 202 may be at angles other than 45°, and the angle may be based on desired operating parameters of the IOL 200.

In operation, a potential difference between the electrode 204 and the optical window 214 may be established by a control circuit, such as the control circuit 108. The potential difference may cause charge to build up on the electrode 204, which may cause the surface energy of the electrode 204, or any encapsulating dielectric layers, to change. The change in surface energy may cause one of the fluids in the cavity to change shape in response. For example, the polar fluid may become more or less attracted to the electrode 204, which may cause the interface 228 to change shape. The change in shape of the interface 228 may cause a lensing effect, which may change an optical power of the IOL 200.

FIG. 3 is a cross-sectional illustration of an electrode 304 in accordance with an embodiment of the disclosure. The electrode 304 may be one example of the electrodes 104 and/or 204. The illustrated embodiment of the electrode 304 includes a face 330, a flange 332, and an underside surface 334. The cross-sectional illustration shows only a portion of the electrode 304, but the electrode may generally complete a full circle, at least with respect to the face 330. In some embodiments, the flange 332 may be a complete circle or a partial circle around the face 330.

The face 330 may be an active surface of the electrowetting electrode and may be formed at a desired angle. For example, the face 330 may be at an oblique angle to the flange 332, and may be in the shape of a conical or a conical frustum. In general, the face 330 may conform to an inner surface of an IOL support structure, such as the inner surface 218. The flange 332 may extend from an edge of the face 330, and may form an area for electrical connection to a driving circuit and/or a power source. In some embodiments, the flange 332 may additionally provide mechanical support for the driving circuits and power source. The underside surface 334 may be in intimate contact with a support structure, such as the support structure 102 and/or 202.

In some embodiments, the face 330 has one or more dielectric layers disposed thereon. For example, a Parylene-based layer and a Fluoropolymer-based layer, in that order, may be deposited on the face 330. Additionally, it may be desirable for the face 330 to have a smooth finish, such as a mirror-like finish. Having a smooth finish may allow for better electrowetting action by an IOL because rough spots on the surface 330 may pin the interface of the two immiscible liquids, such as the interface 228. A pinned interface may prevent the electrowetting lensing from performing as desired.

In some embodiments, the underside surface 334 may desirably be rough or include anchors or nodules extending normal to the surface. The roughness/nodules/anchors may promote adhesion of the electrode 304 to an underlying support structure, which may be formed from a soft, elastic polymer.

The electrode 304 may be formed in various manners. For example, the electrode 304 may be stamped from foil of spring steel or Nitinol, for example. Alternatively, the electrode 304 may be formed via sputtering of a desired metal alloy on a sacrificial form substrate, that may subsequently be removed leaving the electrode 304. The electrode may also be formed using electroforming, where a sacrificial form substrate may be used to electroform the electrode out of a desired metal alloy, and then remove the substrate. It may also be laser cut into rings and in the case of Nitinol be thermoset in a conical shape at a temperature of approximately 500° C.

A thickness of the electrode 304 may depend on various factors of the IOL. In some embodiments, the thickness may be influenced by the material used to form the electrode 304 and a desired bend radius for rolling/folding the IOL prior to insertion into a user's eye. For example, if spring steel is used to form the electrode 304, then the thickness of the electrode 304 may be 5 to 10 microns. For another example, if Nitinol is used to form the electrode 304, then the thickness may be up to 150 microns. The maximum thickness depends on the electrode angle. In some embodiments, having a thicker electrode 304 may ease assembly/manufacturing of the electrode and subsequent IOL.

Figure 4:
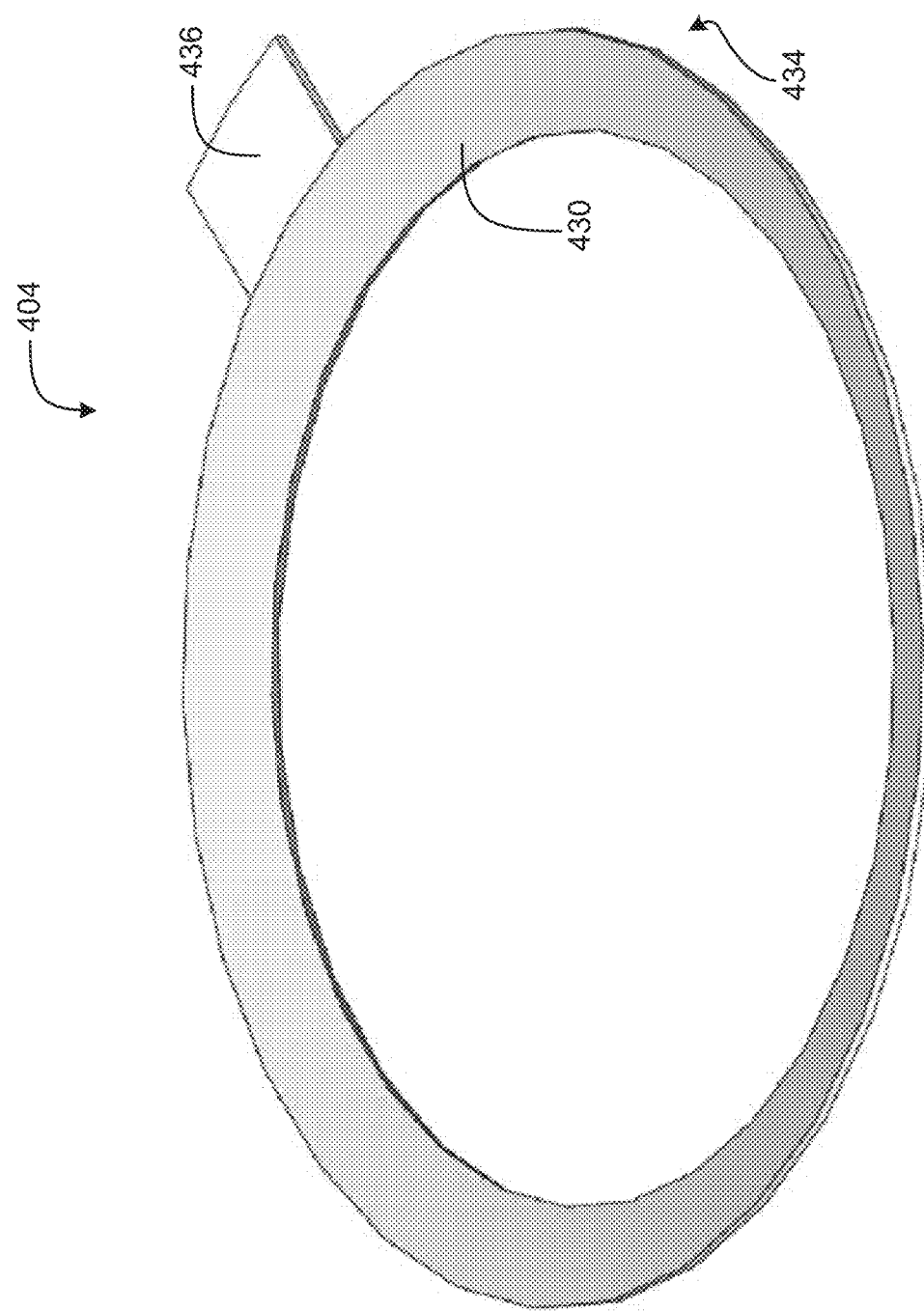
FIG. 4 is a perspective-view illustration of an electrode in accordance with an embodiment of the disclosure.

FIG. 4 is a perspective-view illustration of an electrode 404 in accordance with an embodiment of the disclosure. The electrode 404 may be an example of the electrode 104 and/or 204. The illustrated embodiment of the electrode 404 includes a face 430, a tab 436 and an underside surface 434. The surface 430 and the underside surface 434 may be analogous to like-numbered features of the electrode 304, and will not be discussed in detail for sake of brevity. The tab 436 may be an extension of the electrode 404 providing a location for electrical connection. In some embodiments, the tab 436 may be a flange limited in size and circumference. The electrode 404 may be formed similar to the examples discussed with regards to FIG. 3.

Figure 5:
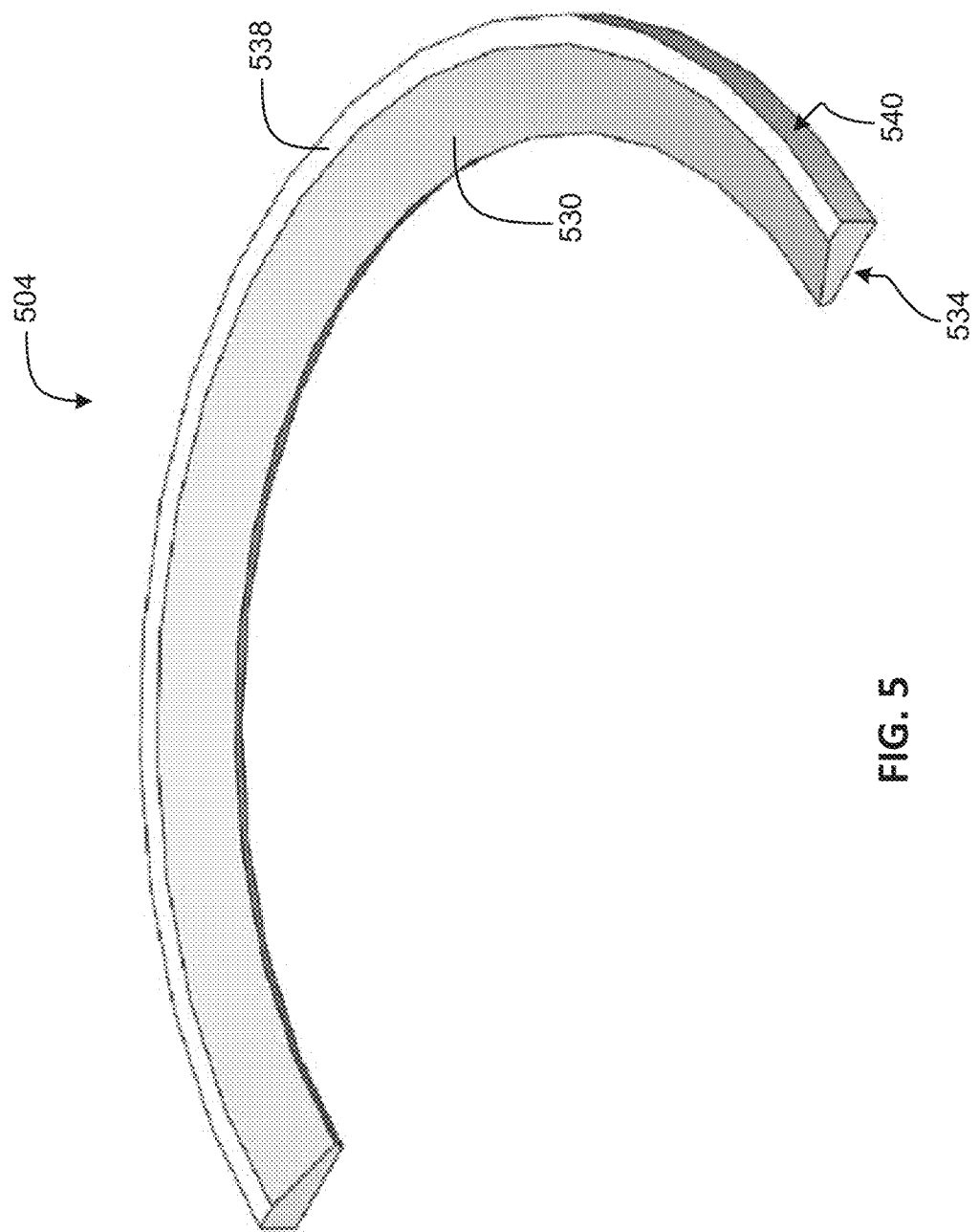
FIG. 5 is a cross-sectional illustration of an electrode in accordance with an embodiment of the present disclosure.

FIG. 5 is a cross-sectional illustration of an electrode 504 in accordance with an embodiment of the present disclosure. The electrode 504 may be an example of the electrode 104 and/or 204. The electrode 504 has many features similar to the electrodes 304 and 404, but a thickness of the electrode 504 is different. In some embodiments, the electrode 504 may be thicker than the electrodes 304, 404 due to how electrode 504 is formed. For example, the electrode 504 may be diamond-point lathed from a stock of Nitinol, or other elastic metal alloy. Single-point diamond turning may provide a smooth surface 530. However, if the electrode 504 is formed from Nitinol, a thicker electrode may be desirable. Of course, a thickness of the electrode 504 may be less than that shown in FIG. 5, and other thicknesses are within the scope of the present disclosure. Further, machining the electrode 504 from stock material may provide a triangular shape to the electrode 504 so that the conical-shaped face 530 is obtained.

The electrode 504 may have a triangular-like cross-section with the surface 530 being in the shape of a conical. The underside surface 534 may extend from the surface 530 to a back surface 540. The back surface 540 may extend between the underside surface 534 and the flange-like surface 538, and may form a thicker portion of the electrode 504. In IOLs that incorporate the electrode 504, the surface 530 may form an aperture similar to the aperture 110 because the electrode 504 may replace the conical frustum-shaped inner surface of the support structure, such as inner surface 218.

The electrode may have two opposite thinner parts. Electronic components are (optionally) placed near the thicker parts. The thinner (integral hinge-like) portions make it easier to fold the lens in half rather than bend it with a uniform radius. The thicker parts remain substantially straight, thus preventing the electronic components and their protective barrier coating from bending and thus damaging. This embodiment is especially effective if the stiffness of the electrode is larger than the stiffness of the polymer lens body around the electrode.

The flange-like surface 538 may provide an electrical coupling area to the electrode 504. Additionally, similar to the electrode 304 and 404, the underside surface 534 may include adhesion promoting structures such as anchors or nodules. Alternatively, the underside 534 may be treated with adhesion promoting materials or processes, e.g., etches or silanes, as well. The electrode 504 may be incorporated into a support structure, such as support structure 102 and/or 202, during molding of the support structure. For example, the electrode 504 may be positioned in a mold prior to injection of the support structure material. The support structure material may conform to the underside 534 and up a wall to the flange 538, and the support structure may mold around any adhesion promoting anchors/nodules to ensure the two components remain attached.

Figure 6:
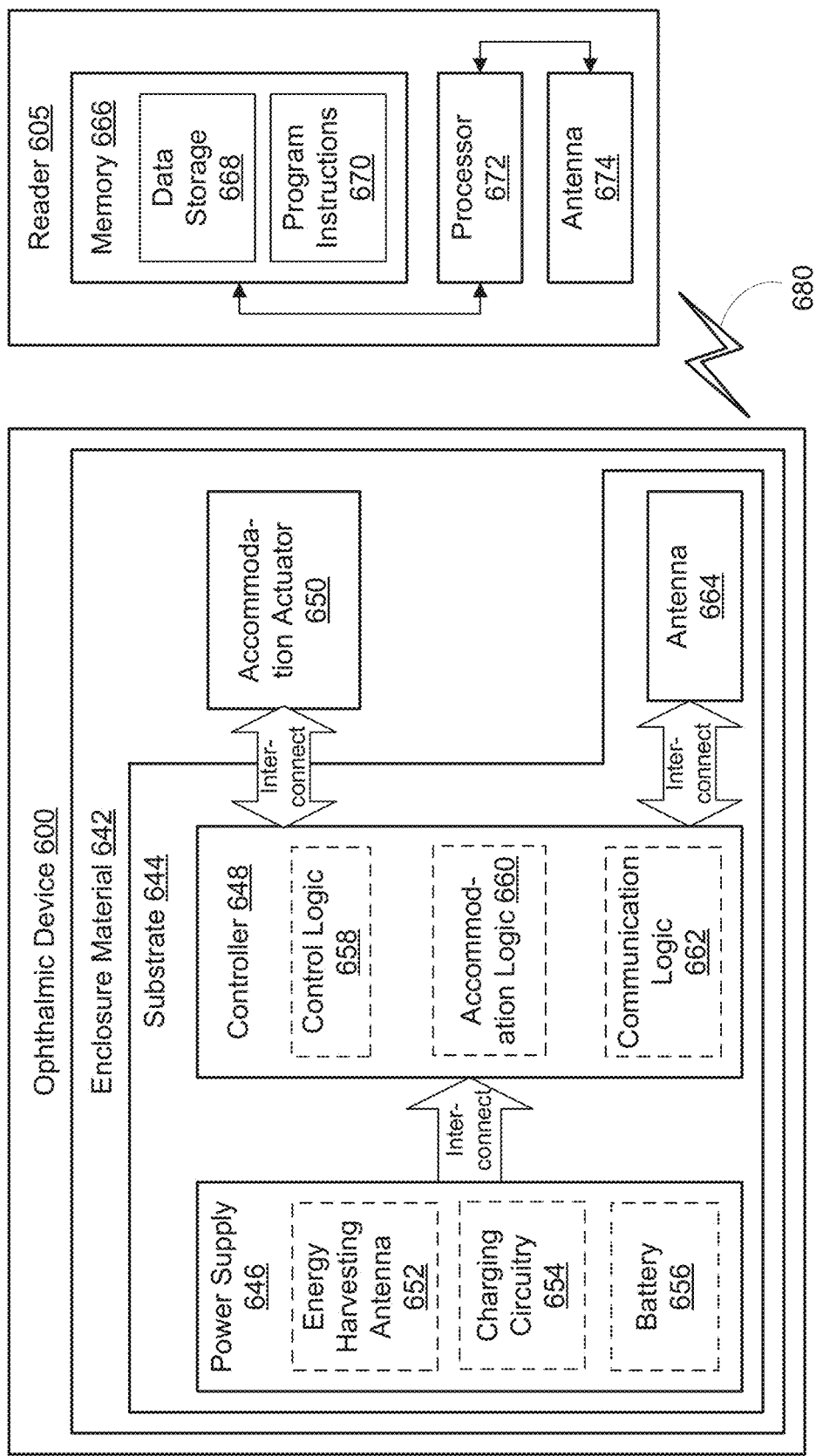
FIG. 6 is a functional block diagram of an ophthalmic device including an elastic electrode in accordance with an embodiment of the present disclosure.

FIG. 6 is a functional block diagram of an ophthalmic device 600 including an elastic electrode in accordance with an embodiment of the present disclosure. Ophthalmic device 600 may be an implantable device, such as an intraocular lens. In the depicted embodiment, ophthalmic device 600 includes an enclosure material 642 formed to be implanted into an eye. A substrate 644 is embedded within or surrounded by enclosure material 642 to provide a mounting surface for a power supply 646, a controller 648, an antenna 664, and various interconnects. The substrate 644 and the associated electronics may be one implementation of the control electronics 108 and an associated substrate, such as the support structure 102. The illustrated embodiment of power supply 646 includes an energy harvesting antenna 652, charging circuitry 654, and a battery 656. The illustrated embodiment of controller 648 includes control logic 658, accommodation logic 660, and communication logic 662. As shown, accommodation actuator 650 is disposed in the enclosure material 642.

Power supply 646 supplies operating voltages to the controller 648 and/or the accommodation actuator 650. Antenna 664 is operated by the controller 648 to communicate information to and/or from ophthalmic device 600. In the illustrated embodiment, antenna 664, controller 648, and power supply 646 are disposed on/in substrate 644, while accommodation actuator 650 is disposed in enclosure material 642 (not in/on substrate 642). However, in other embodiments, the various pieces of circuitry and devices contained in ophthalmic device 600 may be disposed in/on substrate 644 or in enclosure material 642, depending on the specific design of ophthalmic device 600. For example, in one embodiment, accommodation actuator 650 may be disposed on an inner surface of the substrate 642, such as the inner surface 218, and include an elastic electrode, such as the electrodes 104, 204, 304, 404, and/or 504.

Substrate 644 includes one or more surfaces suitable for mounting controller 648, power supply 646, and antenna 664. Substrate 644 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 644 to form circuitry, electrodes, etc. For example, antenna 664 can be formed by depositing a pattern of gold or another conductive material on substrate 644. Similarly, interconnects can be formed by depositing suitable patterns of conductive materials on substrate 644. A combination of resists, masks, and deposition techniques can be employed to pattern materials on substrate 644. Substrate 644 can be a relatively soft material, such as a polymer or another material sufficient to structurally support the circuitry and/or electronics within enclosure material 642 while being flexible enough to being rolled up or folded. Ophthalmic device 600 can alternatively be arranged with a group of unconnected substrates rather than a single substrate 644. For example, controller 648 and power supply 646 can be mounted to one substrate 644, while antenna 664 is mounted to another substrate 644 and the two can be electrically connected via interconnects. Substrate 644 may also be a continuous piece of semiconductor, housing all or some of the aforementioned pieces of device architecture as integrated circuitry.

Substrate 644 can be shaped as a flattened ring with a radial width dimension sufficient to provide a mounting platform for the embedded electronic components. Substrate 644 can have a thickness sufficiently small to allow substrate 644 to be embedded in enclosure material 642 without adversely influencing the profile of ophthalmic device 600. Substrate 644 can have a thickness sufficiently large to provide structural stability suitable for supporting the electronics mounted thereon. For example, substrate 644 can be shaped as a ring with a diameter of about 10 millimeters, a radial width of about 1 millimeter (e.g., an outer radius 1 millimeter larger than an inner radius), and a thickness of about 50 micrometers. In some embodiments, the substrate 644 may encircle at least the optical area associated with the accommodation actuator 650, and may be analogous to the support structures 102 and/or 202. For example, the substrate 644 may be disposed in a peripheral area and in between at least two optical elements, such as optical elements 214 and 216.

In the illustrated embodiment, power supply 646 includes a battery 656 to power the various embedded electronics, including controller 648. Battery 656 may be inductively charged by charging circuitry 654 and energy harvesting antenna 652. In one embodiment, antenna 664 and energy harvesting antenna 652 are independent antennae, which serve their respective functions of energy harvesting and communications. In another embodiment, energy harvesting antenna 652 and antenna 664 are the same physical antenna that are time shared for their respective functions of inductive charging and wireless communications with reader 605. Additionally or alternatively, power supply 646 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 654 may include a rectifier/regulator to condition the captured energy for charging battery 656 and/or directly power controller 648. Charging circuitry 654 may also include one or more energy storage devices to mitigate high frequency variations in energy harvesting antenna 652. For example, one or more energy storage devices (e.g., a capacitor, an inductor, etc.) can be connected to function as a low-pass filter.

Controller 648 contains logic to choreograph the operation of the other embedded components. Control logic 658 controls the general operation of ophthalmic device 600, including providing a logical user interface, power control functionality, etc. Accommodation logic 660 includes logic for receiving signals from sensors monitoring the orientation of the eye, determining the current gaze direction or focal distance of the user, and manipulating accommodation actuator 650 (focal distance of the contact lens) in response to these physical cues. The auto-accommodation can be implemented in real-time based upon feedback from gaze tracking, or permit the user to select specific accommodation regimes (e.g., near-field accommodation for reading, far-field accommodation for regular activities, etc.). Communication logic 662 provides communication protocols for wireless communication with reader 605 via antenna 664. In one embodiment, communication logic 662 provides backscatter communication via antenna 664 when in the presence of an electromagnetic field 680 output from reader 605. In one embodiment, communication logic 662 operates as a smart wireless radio-frequency identification ("RFID") tag that modulates the impedance of antenna 664 for backscatter wireless communications. The various logic modules of controller 648 may be implemented in software/firmware executed on a general purpose microprocessor, in hardware (e.g., application specific integrated circuit), or a combination of both.

Ophthalmic device 600 may include various other embedded electronics and logic modules. For example, a light source or pixel array may be included to provide visible feedback to the user. An accelerometer or gyroscope may be included to provide positional, rotational, directional or acceleration feedback information to controller 648.

The illustrated embodiment also includes reader 605 with a processor 672, an antenna 674, and memory 666. Memory 666 in reader 605 includes data storage 668 and program instructions 670. As shown reader 605 may be disposed outside of ophthalmic device 600, but may be placed in its proximity to charge ophthalmic device 600, send instructions to ophthalmic device 600, and/or extract data from ophthalmic device 600. In one embodiment, reader 605 may resemble a conventional contact lens holder that the user places ophthalmic device 600 in at night to charge, extract data, clean the lens, etc.

External reader 605 includes antenna 674 (or group of more than one antenna) to send and receive wireless signals 680 to and from ophthalmic device 600. External reader 605 also includes a computing system with processor 672 in communication with memory 666. Memory 666 is a non-transitory computer-readable medium that can include, without limitation, magnetic disks, optical disks, organic memory, and/or any other volatile (e.g., RAM) or non-volatile (e.g., ROM) storage system readable by the processor 672. Memory 666 can include a data storage 668 to store indications of data, such as data logs (e.g., user logs), program settings (e.g., to adjust behavior of ophthalmic device 600 and/or external reader 605), etc. Memory 666 can also include program instructions 670 for execution by processor 672 to cause the external reader 605 to perform processes specified by the instructions 670. For example, program instructions 670 can cause external reader 605 to provide a user interface that allows for retrieving information communicated from ophthalmic device 600 or allows transmitting information to ophthalmic device 600 to program or otherwise select operational modes of ophthalmic device 600. External reader 605 can also include one or more hardware components for operating antenna 674 to send and receive wireless signals 680 to and from ophthalmic device 600.

External reader 605 can be a smart phone, digital assistant, or other portable computing device with wireless connectivity sufficient to provide the wireless communication link 680. External reader 605 can also be implemented as an antenna module that can be plugged into a portable computing device, such as in an embodiment where the communication link 680 operates at carrier frequencies not commonly employed in portable computing devices. In some instances, external reader 605 is a special-purpose device configured to be worn relatively near a wearer's eye to allow the wireless communication link 680 to operate with a low power budget. For example, the external reader 605 can be integrated in a piece of jewelry such as a necklace, earing, etc. or integrated in an article of clothing worn near the head, such as a hat, headband, etc.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic device comprising:
   a support structure comprising an elastic polymer;
   first and second optical windows disposed on opposite sides of the support structure;
   two immiscible fluids disposed in a cavity formed by the support structure and the first and second optical windows; and
   a sputtered elastic electrode disposed on an inner surface of the support structure within the cavity, wherein the sputtered elastic electrode is configured not to plastically deform after rolling or bending, and wherein the sputtered elastic electrode is configured to be folded or rolled up without experiencing inelastic deformation upon unfolding or unrolling.

2. The ophthalmic device of claim 1, wherein the sputtered elastic electrode has a thickness in a range of about 5 microns to about 100 microns.

3. The ophthalmic device of claim 1, wherein the support structure is flexibly capable of being rolled up or folded.

4. The ophthalmic device of claim 1, wherein the sputtered elastic electrode is formed from an elastic metal alloy having a minimum yield strain of 0.25%.

5. The ophthalmic device of claim 4, wherein the elastic metal alloy is a shape-memory alloy.

6. The ophthalmic device of claim 4, wherein the elastic metal alloy is valve-metal coated.

7. The ophthalmic device of claim 4, wherein the elastic metal alloy is spring steel.

8. The ophthalmic device of claim 4, wherein the elastic metal alloy is Ti6A14V.

9. The ophthalmic device of claim 1, wherein the sputtered elastic electrode has a conical-shaped surface, wherein the sputtered elastic electrode has a triangular-shaped cross-section having a back surface opposite the conical-shaped surface, the back surface extending from a flange-like top surface to an underside surface, and wherein a thickness of the sputtered elastic electrode at the back surface is thicker than the sputtered elastic electrode along the conical-shaped surface.

10. The ophthalmic device of claim 1, further comprising first and second dielectric layers disposed on the elastic electrode,
wherein the first dielectric layer is formed from a material selected from one of Parylene-C, Parylene-N, Parylene-D, Parylene-HT, and Parylene-AF4, and wherein the second dielectric layer is formed from a fluoropolymer.

11. The ophthalmic device of claim 1, wherein the inner surface has a conical frustum shape and is truncated at an inner most diameter of the conical frustum shape, wherein the support structure further includes first and second recesses formed on a top side and a bottom side, respectively, the first and second recesses encircling an aperture defined by the support structure,
wherein the first recess is defined by a first surface normal to a top surface of the top side, and a second surface normal to the first surface and extending toward the inner surface,
wherein the second recess is defined by a third surface normal to a bottom surface of the bottom side, and a fourth surface normal to the third surface and extending toward the inner surface, and
wherein a portion of the first optical window is disposed in the first recess, and a portion of the second optical window is disposed in the second recess.

12. The ophthalmic device of claim 1, further including control electronics electrically coupled to the sputtered elastic electrode, wherein at least the elastic electrode and the two immiscible fluids form a dynamic optic controlled by the control electronics,
wherein an interface between the two immiscible fluids forms a lens of the dynamic optic, and
wherein the two immiscible fluids include an oil and an electrolyte.

* * * * *